United States Patent [19]
Baird et al.

[11] 3,992,410
[45] Nov. 16, 1976

[54] PROCESS FOR MANUFACTURING THIOPHENE DERIVATIVES

[75] Inventors: David Boyd Baird; Brian Ribbons Fishwick; Ian Knowles Barben, all of Manchester, England; John Murray Holland, deceased, late of Bury, England, by Susan Holland, sole administratrix

[73] Assignee: Imperial Chemical Industries Limited, London, England

[22] Filed: June 4, 1975

[21] Appl. No.: 583,764

[30] Foreign Application Priority Data

June 11, 1974 United Kingdom............... 25847/74

[52] U.S. Cl..................... 260/329 S; 260/329 AM; 260/329 HS; 260/329 F
[51] Int. Cl.².................................. C07D 333/00
[58] Field of Search...... 260/332.8, 329 AM, 329 S, 260/329 SH, 329 F

[56] References Cited
UNITED STATES PATENTS 2,570,083   10/1951   Wadley............................ 260/332.8

*Primary Examiner*—James O. Thomas, Jr.
*Assistant Examiner*—A. Siegel
*Attorney, Agent, or Firm*—Cushman, Darby & Cushman

[57] ABSTRACT

Process for the manufacture of salts of 2-aminothiophenes having the formula:

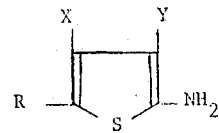

wherein R, X and Y are each independently a hydrogen atom, an alkyl radical or an optionally substituted aryl radical, or a thienyl or furyl radical or either R and X or X and Y together form a chain or methylene groups to form a 5- or 6- membered fused ring system, which comprises treating the corresponding compound of the formula:

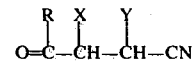

with hydrogen sulphide in the presence of an acid and in the presence of an organic solvent, and the use of the said salts as diazo components in the manufacture of azo dyestuffs.

3 Claims, No Drawings

PROCESS FOR MANUFACTURING THIOPHENE DERIVATIVES

This invention relates to a process for the manufacture of salts of 2-aminothiophenes.

According to the invention there is provided a process for the manufacture of salts of 2-aminothiophenes having the formula:

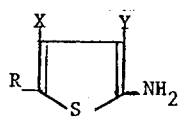

wherein R, X and Y are each independently a hydrogen atom, an alkyl radical or an optionally substituted aryl radical, or a thienyl or furyl radical or either R and X or X and $Y^1$ together form a chain of methylene groups to form a 5- or 6-membered fused ring system, which comprises treating the corresponding compound of the formula:

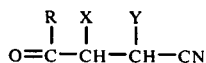   Formula I with hydrogen sulphide in the presence of an acid and in the presence of an organic solvent.

The alkyl radicals represented by R, X and Y are preferably lower alkyl radicals containing from 1 to 4 carbon atoms such as methyl, ethyl, propyl and butyl radicals. The optionally substituted aryl radicals are preferably optionally substituted phenyl radicals such as phenyl, tolyl, xylyl, chlorophenyl, bromophenyl, nitrophenyl, methoxyphenyl, ethoxyphenyl, methoxycarbonylphenyl, ethoxycarbonylphenyl, lower alkylcarbonylphenyl such as acetylphenyl, cyanophenyl, lower alkylsulphonylphenyl such as methylsulphonylphenyl, carbamoylphenyl and sulphamoylphenyl and N-lower alkyl and N:N-di(lower alkyl)derivatives thereof.

Preferably Y represents hydrogen. X preferably represents methyl and, above all, hydrogen. Preferably R represents hydrogen, and, above all, optionally substituted phenyl.

The process of the invention can be conveniently carried out by passing a stream of gaseous hydrogen sulphide through a solution of the compound of Formula I in an organic solvent which also contains the acid, the reaction being carried out at a temperature between −20° C and the boiling point of the reaction medium. At the conclusion of the reaction the resulting salt of the 2-aminothiophene is isolated by conventional methods, for example by dilution with an organic liquid in which the salt is insoluble. Preferably the organic solvent used for the reaction medium is one in which the said salt is substantially insoluble, so that the said salt separates out as it is formed and can be directly isolated by filtration.

As examples of the said organic solvents there may be mentioned hydrocarbons such as toluene, esters such as ethyl acetate, ketones such as acetone, alcohols such as n-butanol, isopropanol, ethanol and methanol, ethers such as dioxan, tetrahydrofuran, liquid carboxylic acids such as acetic acid, and polar aprotic solvents such as dimethylformamide. Whilst the said organic solvents are preferably anhydrous it is found in practice that the presence of a small amount of water is not detrimental to the reaction.

The amount of acid present in the reaction is not critical provided that at least one mole of acid is used for each mole of the compound of Formula I. Preferably the acids used in the reaction are strong acids having a negative pKa value, and as examples of such acids there may be mentioned hydrogen chloride, hydrogen bromide, sulphuric acid and benzene sulphonic acid.

The compounds of Formula I used in the process are aldehydes or ketones depending on whether or not R is a hydrogen atom, but if desired such compounds can be used in the form of their reaction products with alcohols, i.e. the corresponding ketals or acetals, which are reconverted to the parent aldehyde or ketone during the reaction.

The compounds of Formula I or their acetals or ketals can be themselves obtained by a number of known methods, for example by:

a. Reaction of an α:β-unsaturated nitrile with carbon monoxide and hydrogen in the presence of a cobalt catalyst b. By Mannich Reaction on ketones in the presence of formaldehyde and dimethylamine hydrochloride followed by reaction with cyanide ions.

c. By reacting a ketal or acetal corresponding to a compound of the formula

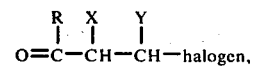

wherein halogen is chlorine or bromine with potassium cyanide.

d. By reacting α:β-unsaturated aldehydes or ketones with hydrogen cyanide.

As specific examples of the compounds of Formula I there may be mentioned β-benzoylpropiononitrile, levulinonitrile β-cyanopropionaldehyde, 2-oxocyclohexaneacetonitrile, α-phenyl levulinonitrile and α-phenylβ-benzoylpropionitrile.

The salts of the 2-aminothiophenes produced by the process of the invention are valuable as diazo components in the production of azo dyestuffs.

Alternatively the said salts can be converted to other thiophene derivatives in conventional manner. For example they can be converted to 2-acylamino derivatives by treatment with an acylating agent such as acetic anhydride in the presence of a base, and such reactions can be carried out, if desired, without intermediate isolation of the said salt from the reaction mixture of the present process.

The invention is illustrated but not limited by the following Examples in which the parts and percentages are by weight.

EXAMPLE 1

Slow streams of gaseous hydrogen chloride and gaseous hydrogen sulphide are simultaneously bubbled for 7 hours through a stirred solution of 7.95 parts of β-benzoylpropionitrile in 100 parts of methanol at 10° to 20° C. The mixture is then stirred overnight and the precipitated hydrochloride of 2-amino-phenylthiophene is filtered off, washed with methanol and dried. The yield is 7.6 parts (72%).

The identity of the product was confirmed as follows:

A mixture of 1 part of the product, 10 parts of water, 4 parts of acetic anhydride and 10 parts of an 8% aqueous solution of sodium hydroxide was stirred for 1 hour at 20° C, and the precipitated solid filtered off, washed with water and dried. This solid was found to be identical by (a) melting point and mixed melting point, (b) thin layer chromatography and (c) Infra Red Spectra, with an authentic sample of 2-acetylamino-5-phenylthiophene which had been prepared by a known method.

In place of the 7.95 parts of β-benzoylpropiononitrile used in Example 1 there are used equivalent amounts of the ketones listed in the second column of the following Table whereby there are obtained the hydrochlorides of the compounds listed in the third column of the Table.

wherein Y is hydrogen, X is selected from the group consisting of hydrogen and lower alkyl, and R is selected from the group consisting of hydrogen, lower alkyl, phenyl, tolyl, xylyl, chlorophenyl, bromophenyl, dichlorophenyl, nitrophenyl, cyanophenyl, lower alkylsulphonylphenyl and ethoxycarbonylphenyl, thienyl and furyl, or X and Y together comprise a chain of methylene groups to form a 5- or 6-membered fused ring system, which comprises treating a compound of the formula:

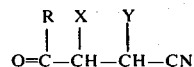

I

| Example | Ketone | Compound |
|---|---|---|
| 2 | β-(4-methylbenzoyl)propionitrile | 2-amino-5-(4'-methylphenyl)thiophene |
| 3 | β-(2-methylbenzoyl)propionitrile | 2-amino-5-(2'-methylphenyl)thiophene |
| 4 | β(2:4-dimethylbenzoyl)propionitrile | 2-amino-5-(2':4'-dimethylphenyl)thiophene |
| 5 | β-(4-chlorobenzoyl)propionitrile | 2-amino-5-(4'-chlorophenyl)thiophene |
| 6 | β-(2-bromobenzoyl)propionitrile | 2-amino-5-(2'-bromophenyl)thiophene |
| 7 | β-(2:5-dichlorobenzoyl)propionitrile | 2-amino-5-(2':5':-dichlorophenyl)thiophene |
| 8 | β-(4-nitrobenzoyl)propionitrile | 2-amino-5-(4'-nitrophenyl)thiophene |
| 9 | β-(3-cyanobenzoyl)propionitrile | 2-amino-5-(3'-cyanophenyl)thiophene |
| 10 | β-(3-ethoxycarbonylbenzoyl)propionitrile | 2-amino-5-(3'-ethoxycarbonylphenyl)thiophene |
| 11 | β-(3-methylsulphonylbenzoyl) propionitrile | 2-amino-5-(3'-methylsulphonylphenyl)thiophene |
| 12 | β-benzoylbutyronitrile | 2-amino-4-methyl-5-phenylthiophene |

EXAMPLE 13

A slow stream of hydrogen chloride gas is bubbled for 10 minutes through a solution of 13.7 parts of 2-oxo-cyclohexylacetonitrile in 100 parts of methanol at 0° to 10° C. A slow stream of hydrogen sulphide gas is then bubbled through the mixture for 8 hours at 0° to 10° C. The mixture is then allowed to stand at room temperature and the hydrochloride of 2-amino-4:5:6:7-tetrahydrobenzo-b-thiophene which separates out is filtered off and dried.

Identity of this product was confirmed by acetylation, the resulting acetyl derivative being identical with 2-acetylamino-4:5:6:7-tetrahydrobenzo-b-thiophene prepared by an established method.

We claim:
1. A process for the manufacture of a salt of a 2-aminothiophene of the formula:

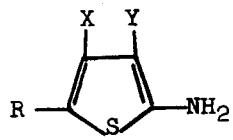

with hydrogen sulphide in the presence of an acid selected from the group consisting of hydrogen chloride, hydrogen bromide, sulfuric acid and benzene sulphonic acid, in an amount of at least one mole of said acid per mole of formula 1 to form said salt and in an organic solvent medium at a temperature between −20° C and the boiling point of the reaction mixture.

2. A process as claimed in claim 1 wherein the starting material used in the process is of the formula:

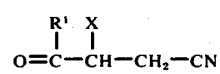

wherein X is selected from the group consisting of hydrogen and lower alkyl, and R¹ is selected from the group consisting of hydrogen phenyl, tolyl, xylyl, chlorophenyl, bromophenyl, dichlorophenyl, nitrophenyl, cyanophenyl, lower alkylsulphonylphenyl and ethoxycarbonylphenyl.

3. A process as claimed in claim 1, wherein said acid is hydrogen chloride.

* * * * *